(12) United States Patent
Okoniewski

(10) Patent No.: US 8,663,737 B2
(45) Date of Patent: Mar. 4, 2014

(54) LUBRICIOUS COATINGS

(75) Inventor: Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 13/358,598

(22) Filed: Jan. 26, 2012

(65) Prior Publication Data

US 2012/0128874 A1   May 24, 2012

Related U.S. Application Data

(62) Division of application No. 12/165,834, filed on Jul. 1, 2008, now Pat. No. 8,128,599.

(60) Provisional application No. 60/961,365, filed on Jul. 20, 2007.

(51) Int. Cl.
*F16C 33/72* (2006.01)
*F16C 33/74* (2006.01)
*F16C 33/76* (2006.01)

(52) U.S. Cl.
USPC ............ 427/256; 427/11; 427/282; 427/287; 604/164.01; 604/167.06; 277/590; 277/628; 277/644; 277/648; 277/649

(58) Field of Classification Search
None
See application file for complete search history.

(56) References Cited

U.S. PATENT DOCUMENTS

| 5,091,205 | A | 2/1992 | Fan |
| 5,391,153 | A | 2/1995 | Haber et al. |
| 5,540,661 | A | 7/1996 | Tomisaka et al. |
| 5,902,329 | A | 5/1999 | Hoffmann et al. |
| 5,997,515 | A | 12/1999 | de la Torre et al. |
| 6,616,765 | B1 | 9/2003 | Castro et al. |
| 6,656,517 | B2 | 12/2003 | Michal et al. |
| 6,702,787 | B2 | 3/2004 | Racenet et al. |
| 6,866,656 | B2 | 3/2005 | Tingey et al. |
| 7,344,499 | B1 | 3/2008 | Prausnitz et al. |
| 2003/0102632 | A1* | 6/2003 | Duta et al. ............. 277/500 |
| 2003/0143315 | A1 | 7/2003 | Pui et al. |
| 2004/0024448 | A1 | 2/2004 | Chang et al. |
| 2005/0171479 | A1 | 8/2005 | Hruska et al. |
| 2006/0173421 | A1 | 8/2006 | Weber et al. |
| 2006/0253077 | A1 | 11/2006 | Smith |
| 2006/0264905 | A1 | 11/2006 | Eskridge et al. |
| 2007/0085232 | A1 | 4/2007 | Brustad et al. |
| 2007/0148697 | A1 | 6/2007 | Delaney, Jr. et al. |

FOREIGN PATENT DOCUMENTS

| EP | 0716834 | 6/1996 |
| WO | WO 95/04564 | 2/1995 |
| WO | WO 00/10622 | 3/2000 |

OTHER PUBLICATIONS

European Search Report for corresponding EP08252390 date of mailing is Apr. 29, 2011 (3 pgs).

* cited by examiner

*Primary Examiner* — Michael Cleveland
*Assistant Examiner* — Lisha Jiang

(57) ABSTRACT

The present disclosure provides substrates having a lubricious coating thereon. The substrate may be flexible and include, in embodiments, a medical device. The lubricious coating, in embodiments, is applied in a pattern so that the coating avoids delamination and/or fracturing which might otherwise occur as the substrate flexes and/or stretches.

16 Claims, 5 Drawing Sheets

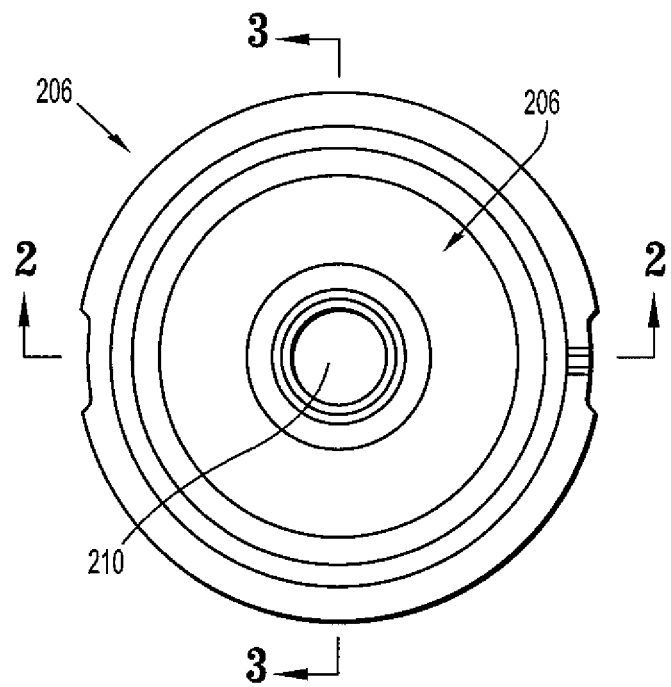
FIG. 1
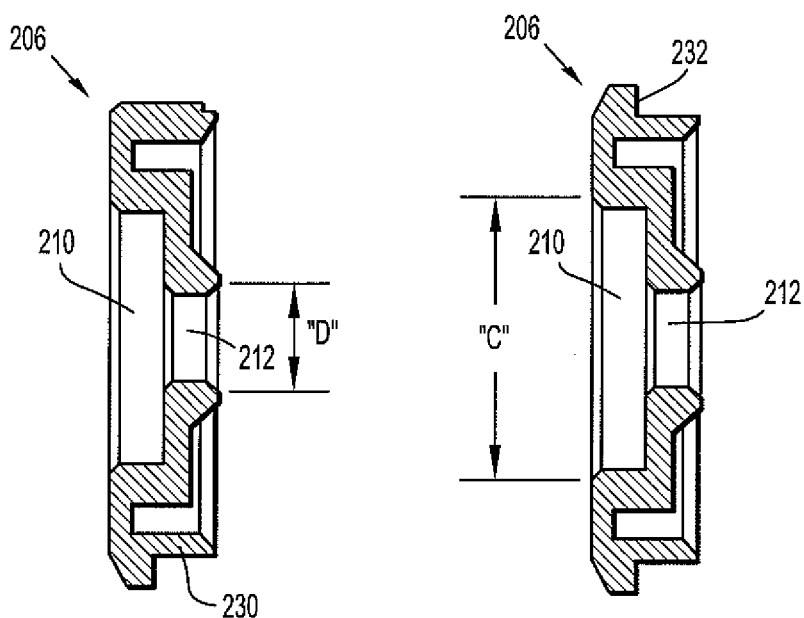
FIG. 2        FIG. 3

US 8,663,737 B2

LUBRICIOUS COATINGS

CROSS-REFERENCE TO RELATED APPLICATIONS

This application is a divisional application of U.S. Ser. No. 12/165,834 (now U.S. Pat. No. 8,128,599), filed Jul. 1, 2008, which claims the benefit of and priority to U.S. Application Ser. No. 60/961,365, filed on Jul. 20, 2007, all of which is incorporated herein in its entirety by reference.

TECHNICAL FIELD

The present disclosure relates to lubricious coatings for substrates, in embodiments medical devices. The lubricious coatings of the present disclosure may, in embodiments, be applied in a matrix pattern.

BACKGROUND

The application of lubricious coatings to medical devices is within the purview of those skilled in the art. For example, metallic devices such as surgical needles may have lubricious coatings applied thereto to facilitate the passage of the needle through tissue. Other medical devices, including those which may come into contact with tissue or additional medical devices, may similarly benefit from the application of a lubricious coating thereto, for example, to enhance the passage of the device through tissue or the passage of one medical device in contact with a second medical device, for example, the passage of a catheter through a cannula.

Yet other medical devices which may benefit from a lubricious coating include seals utilized with access ports in connection with minimally invasive surgical procedures such as endoscopic and laparoscopic procedures. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures often employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum. Such devices, including cannulas, seals, and instruments passing therethrough, may benefit from the application of a lubricious coating thereon.

One issue which may arise with the application of a lubricious coating to a substrate, especially a flexible substrate, is the lubricious coating may fracture or delaminate from the substrate to which it is applied. Thus, a lubricious coating capable of avoiding delamination or fracturing would be desirable.

SUMMARY

The present disclosure provides lubricious coatings for devices which may, in embodiments, be applied in a matrix pattern. In embodiments, the present disclosure provides articles including a substrate, and a patterned lubricious coating including a dot matrix pattern on at least a portion of the substrate.

In embodiments, methods of the present disclosure may include providing a substrate, and applying to the substrate a lubricious coating in a dot matrix pattern.

Suitable substrates include, in embodiments, medical devices.

BRIEF DESCRIPTION OF THE DRAWINGS

Embodiments of the present disclosure will be readily appreciated by reference to the drawings wherein:

FIG. 1 is a top plan view of a cover of a seal assembly;

FIGS. 2-3 are cross-sectional views of the cover of the seal assembly respectively taken along lines 5-5 and 6-6 of FIG. 1;

DETAILED DESCRIPTION

Figure 4:
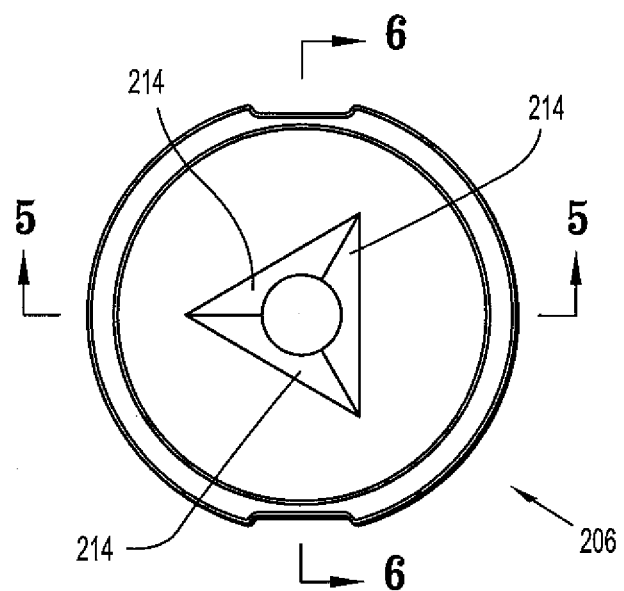
FIG. 4 is a top plan view of an alternate embodiment of the cover of the seal assembly.

Substrates of the present disclosure possess a lubricious coating thereon. In accordance with the present disclosure, any suitable lubricious coating may be applied to a substrate, such as a medical device. Such coatings include, for example, cyanoacrylates; epoxies; hydrophilic polymers including hydrogels; polyalkylene oxides including polyethylene oxide, polypropylene oxide, polyethylene oxide/polypropylene oxide copolymers, polyethylene glycol, polypropylene glycol; urethanes such as polyurethane; siloxanes, including cyclosiloxanes, polyalkylsiloxanes, and polydialkylsiloxanes such as polydimethylsiloxanes, polydiethylsiloxanes, polydipropylsiloxanes, polydibutylsiloxanes; parylenes including parylene N, parylene C, parylene D, and parylene HT; combinations thereof, and the like.

The lubricious coating may be applied utilizing any method within the purview of those skilled in the art. In embodiments, the materials utilized to form the coatings may be applied in a powder or liquid form. The coating materials may be applied to a substrate in any suitable pattern, including dots, stripes, spirals, combinations thereof, and the like. In some embodiments, it may be desirable to apply the lubricious coating in a dot pattern, sometimes referred to herein as a dot matrix pattern. The dots may be circular, oblong, square, hexagonal, or any other suitable geometric shape and may be applied individually or simultaneously. The dots may be configured so that they line up in rows, are offset between rows, or are in a completely random pattern. The spacing, pattern, and geometry utilized in applying the coating, in some cases as dots, may vary to accommodate the geometry of the substrate to which the coating is applied. The resulting coating may be referred to, in embodiments, as a patterned coating.

Any means within the purview of those skilled in the art may be utilized to apply the lubricious coating materials to a substrate. In some embodiments, suitable methods which may be utilized to apply lubricious coating materials include gravure coating, spray coating, melt blowing, thermal/heat transfer, vapor deposition, deposition by nozzle, flexographic printing techniques, such as offset flexographic printing, screen printing, laserjet or inkjet, combinations thereof, and the like. Relevant parameters related to application include, but are not limited to, nozzle geometry of a spray device, time necessary for application, pressure, temperature, humidity, curing time and temperature, wavelength where curing includes the application of light, the state of the substrate, including its natural or elongated state, the coating thickness, individual dot geometry and size, spacing of the dots, and the like.

As noted above, in some embodiments the materials utilized to form the coatings of the present disclosure may be applied in powder form. In other embodiments, the materials utilized to form the coatings of the present disclosure may be applied in liquid form. Where the materials are applied as liquids, it may be desirable to form a coating solution by placing the materials utilized to form the coatings of the present disclosure in a suitable solvent. Any solvent within the purview of those skilled in the art may be utilized; however, as would be apparent to one skilled in the art, the solvent should be compatible with both the coating materials and the substrate to be coated and should not degrade either during application of the coating materials. Examples of suitable solvents include tetrahydrofuran, chlorinated hydrocarbons such as methylene chloride, alcohols such as methanol, ethanol, and propanol, chloroform, 1,2-dichloro-ethane, aliphatic hydrocarbons such as hexane, heptene, and ethyl acetate, combinations thereof, and the like.

Where the coating materials are applied as part of a solution, the coating solution may contain from about 30 to about 70 weight percent solvent, in embodiments from about 45 to about 55 weight percent solvent. If desired, the coating solution can optionally contain additional components such as dyes, antibiotics, antiseptics, growth factors, anti-inflammatory agents, combinations thereof, and the like.

Once applied, in some embodiments the materials utilized to form the patterned coatings of the present disclosure may be further treated to further enhance formation of the coating. Methods for treating the materials utilized to form coatings of the present disclosure are within the purview of those skilled in the art. For example, in some embodiments it may be desirable to cure the coating materials to enhance their lubricity and rigidity. Such methods for curing may include heating to suitable temperatures, which will depend upon the materials utilized to form the coatings herein. This may be desirable where the coating materials are applied in powder form, or where the coating materials are applied in solution and it is desired to remove the solvent utilized to form the solution. For example, once applied, the coating material and the now-coated substrate may be heated to a temperature of from about 80° F. to about 350° F., in embodiments from about 120° F. to about 250° F. A vacuum may be applied in embodiments to accelerate curing. In other embodiments, solvents utilized to apply the coatings may simply evaporate upon application, leaving the lubricious coating material in the applied pattern upon the substrate.

In other embodiments, curing may occur by the application of a light source including ultraviolet light or light from a coherent light source such as a laser source. Suitable UV light sources may be at a wavelength of from about 80 nm to about 400 nm, in embodiments from about 290 nm to about 380 nm. Suitable coherent light sources such as a laser may be applied at a wavelength of from about 80 nm to about 1540 nm, in embodiments from about 290 nm to about 400 nm.

In yet other embodiments, a mask material may be applied to a substrate to be coated, wherein the mask has a configuration of the dot pattern to be applied to the surface of the substrate. The masking material is first applied to the substrate, having openings therein corresponding to the pattern for the dots to be applied the substrate. The coating materials may then be applied utilizing any method within the purview of those skilled in the art, including those noted above, as well as dipping, the substrate into the coating material. The coating materials may then be allowed to cure, if necessary, after which time the masking material may be removed, leaving the dot pattern of coating material on the surface of the substrate.

Substrates possessing a lubricious coating of the present disclosure in a pattern may have a coating-free surface area of more than about 75% of the surface, in embodiments a coating-free surface area of from about 75% to about 99% of the surface, in other embodiments a coating-free surface area of from about 80% to about 90%.

In embodiments, it may be desirable to apply the coating in a pattern, in embodiments as dots, so that any surface that is to slide against the substrate only comes into contact with the lubricious coating applied thereon, and does not come into contact with the surface of the substrate having a higher coefficient of friction, to which no coating has been applied. The spacing and pattern of the lubricious coating applied as dots may also be varied to maintain elongation and flexibility of the substrate, especially an elastomeric substrate. In this manner, the substrate may be able to continue to elongate between the lubricious coating applied as dots. In embodiments, a single dot of lubricious coating material may have a ratio of height to diameter not greater than about 2:1, in embodiments from about 0.05:1 to about 2:1, in other embodiments from about 0.1:1 to about 1:1.

Thus, a coating of the present disclosure may be utilized to transform the surface of a substrate having a surface with a higher coefficient of friction into a surface with a lower coefficient of friction. While the coating material itself is rigid, devices made of flexible substrates possessing a coating of the present disclosure may remain flexible without substantial fracturing of the coating or delamination of the coating from the substrate.

As noted above, in some embodiments suitable substrates to be coated with a patterned coating of the present disclosure include medical devices. Examples of such medical devices include, but are not limited to, seals, delivery devices such as staplers, clip appliers, energy suppliers, and the like, cannulas, obturators, catheters, filaments including monofilament and multi-filament sutures, surgical clips and other fasteners, staples, pins, screws, prosthetic devices, drug delivery devices, meshes or fabrics, anastomosis rings, adhesives, sealants, and other implantable devices.

In some embodiments, a medical device having a patterned coating in accordance with the present disclosure may include a surgical seal, a cannula for use with such a seal, or both. For example, a surgical seal system may be utilized with a cannula assembly having a cannula housing and a cannula sleeve extending from the cannula housing. Examples of such systems include, but are not limited to, those disclosed in U.S. Patent Application Publication No. 2006/0253077, the entire disclosure of which is incorporated by reference herein. A patterned lubricious coating of the present disclosure may be applied on a portion of any surface of any component of such a system.

For example, a surgical seal assembly may include a seal assembly mountable to the cannula housing and an adapter assembly adapted for releasably coupling to the seal assembly. The seal assembly may include a seal housing and a seal.

The seal defines inner portions adapted to form a substantial seal about an instrument with a first cross-sectional dimension. The seal assembly includes a seal mount. The seal is molded to the seal mount. The seal assembly may be releasably mountable to the cannula housing. A seal, cannula, and/or an instrument passing therethrough may possess a patterned coating of the present disclosure.

In other embodiments, a surgical seal system for use with a cannula assembly having a cannula housing and a cannula sleeve extending from the cannula housing is provided. The surgical seal assembly includes a seal housing defining a seal axis and having a seal mount at least partially positionable within the cannula housing. The seal mount may have a resilient seal member molded thereto. The seal member defines inner portions adapted to form a substantial seal about an instrument. A cover is adapted for mounting to the cannula housing to secure the seal mount within the cannula housing. The cover may include a cover opening for permitting passage of the instrument. The cover may include a plurality of intersecting entry surfaces. The entry surfaces may be obliquely arranged relative to the seal axis and are adapted to guide the instrument through the opening of the cover. The seal and/or the seal cover may possess a patterned coating of the present disclosure. The seal mount may include a plurality of peripherally disposed apertures whereby anchoring segments of the seal member are received within the apertures to facilitate securing of the seal member to the seal mount.

In embodiments, a suitable seal system may accommodate objects of varying diameters, e.g., instruments from about 3 mm to about 15 mm, and may provide the capability of forming a gas tight seal with each instrument when inserted.

Any seal, cannula, seal cover, instrument for use therewith, and the like may possess a patterned coating of the present disclosure. In some embodiments, a seal system may include a first seal assembly which is releasably mountable to the housing of a cannula. The first seal assembly may be adapted to form a seal about a first instrument having a first cross-section or diameter. The seal system may also include an adapter assembly as disclosed in U.S. Patent Application Publication No. 2006/0253077, which may be connected or attached to the cannula sleeve of the cannula. The adapter assembly may be adapted to mount over the seal assembly to form a seal about a second instrument having a second cross-section or diameter different than the first instrument, e.g., a smaller-diameter instrument. Any of the seal assembly, adapter assembly, cannula, cannula sleeve, and the like may possess a patterned coating of the present disclosure.

The cannula assembly may be any conventional cannula assembly suitable for the intended purpose of accessing a body cavity to permit introduction of instruments therethrough. The cannula assembly may be adapted for use in laparoscopic surgery where the peritoneal cavity is insufflated with a suitable gas, e.g., $CO_2$, to raise the cavity wall from the internal organs therein. The cannula assembly may be used with an obturator assembly, which is an elongate instrument positionable within the cannula assembly. The obturator assembly may have a sharp end or a blunt end and is utilized to pass through, e.g., abdominal tissue, to facilitate introduction of the cannula assembly within the abdominal cavity. An obturator may also possess a patterned coating of the present disclosure on an external surface thereof to facilitate the passage of the obturator through tissue and the cannula assembly.

Once access to the abdominal cavity is achieved, the obturator assembly may be removed from the cannula assembly to permit subsequent introduction of the surgical instrumentation through the cannula assembly to perform the procedure.

As noted above, in embodiments a seal assembly may possess an adapter assembly, including an adapter assembly as disclosed in U.S. Patent Application Publication No. 2006/0253077 which includes an adapter body having an adapter seal defining internal portions adapted to form a substantial seal about an instrument with a second cross-sectional dimension different from the first cross-sectional dimension. The adapter body may include a manual release tab. The release tab may be dimensioned for manual engagement by a surgeon to facilitate releasing of the adapter body from the seal assembly. The adapter body includes an entry surface which generally tapers toward a central axis of the adapter body. The tapered surface may be generally frusto-conical in configuration. The adapter body may include an outer wall. The outer wall is adapted for positioning over the seal housing. In some embodiments, the outer wall of the adapter body may be positionable over a peripheral ledge of the seal housing. In some embodiments, the adapter body may be made of a suitable elastomeric material. Any surface of the adapter assembly, including the entry surface, may possess a patterned coating of the present disclosure.

In other embodiments, an adapter apparatus adapted for releasably coupling to a cannula assembly having a cannula housing and a cannula sleeve is provided. The adapter apparatus includes an adapter body having an adapter seal defining internal portions adapted to form a substantial seal about an instrument and adapted for mounting to the cannula sleeve. Such an adapter body or cannula sleeve may similarly possess a patterned coating of the present disclosure.

In embodiments, a seal may possess a patterned coating of the present disclosure. In embodiments, the seal may be used with an instrument having a first diameter of from about 3 mm to about 7 mm, in some embodiments about 5 mm. In other embodiments, the seal may be used with a trocar having a diameter from about 3 mm to about 15 mm. Alternatively, a seal may be used to form a seal around a surgeon's arm. In embodiments, the seal may be contained in a seal housing as part of a cannula assembly. Such a seal housing may include a seal cover and seal support, with a seal between the cover and support.

As depicted in FIGS. 1-3, seal cover 206 may have a stepped configuration defining proximal opening 210 and distal opening 210 distal of the proximal opening 208. Proximal opening 210 is substantially constant in diameter defining a diameter "C" of from about 4 mm to about 8 mm. Distal opening 212 defines a diameter "D" of from about 2 mm to about 6 mm. Proximal opening 210 and distal opening 212 may be smaller or larger to accommodate smaller or larger size instruments.

Figure 5:
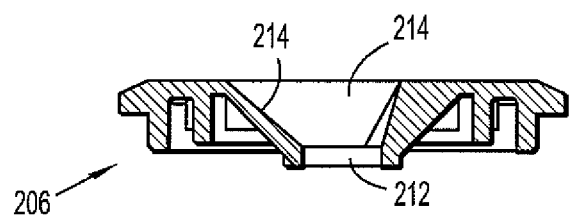
FIGS. 5-6 are cross-sectional views of the cover of FIG. 4 respectively taken along lines 8-8 and 9-9 of FIG. 4.
Figure 6:
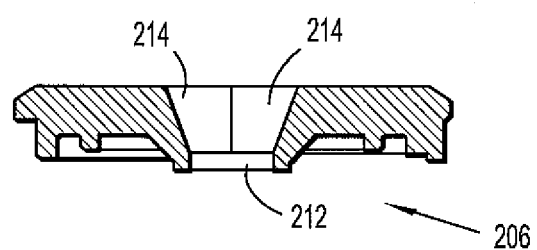
Figure 7:
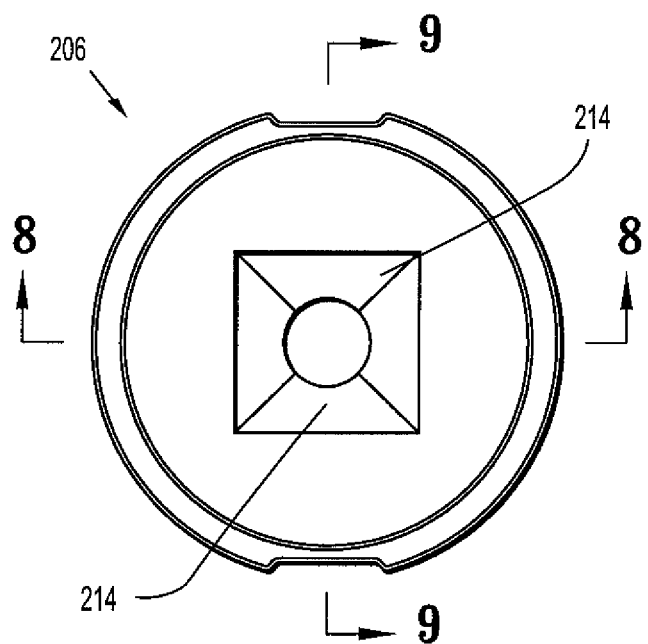
FIG. 7 is a top plan view of the another alternate embodiment of the cover of the seal assembly.
Figure 8:
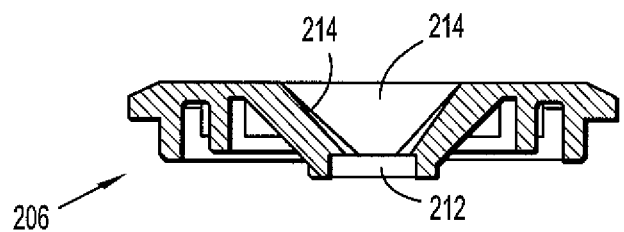
FIGS. 8-9 are cross-sectional views of the cover of FIG. 7 respectively taken along lines 11-11 and 12-12 of FIG. 7.
Figure 9:
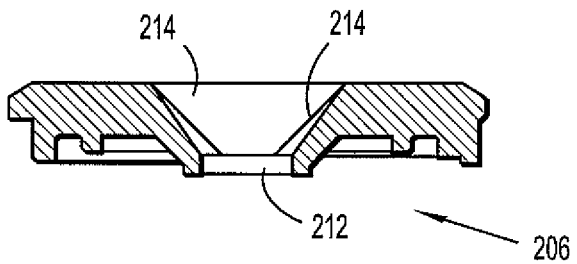
Figure 10:
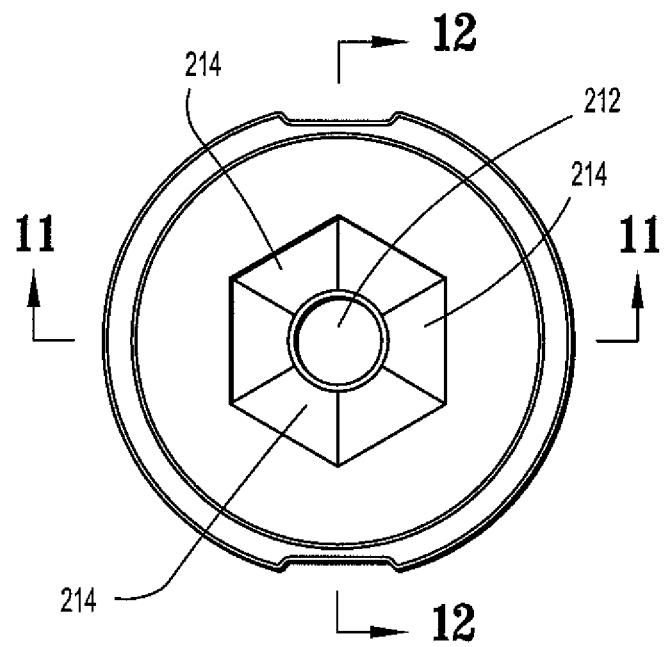
FIG. 10 is a top plan view of yet another alternate embodiment of the cover of the seal assembly.
Figure 11:
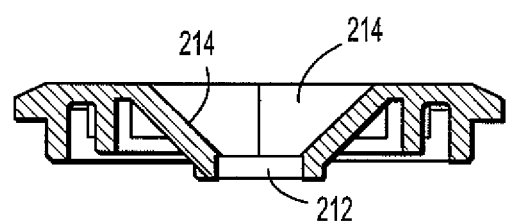
FIGS. 11-12 are cross-sectional views of the cover of FIG. 10 respectively taken along lines 14-14 and 15-15 of FIG. 10.
Figure 12:
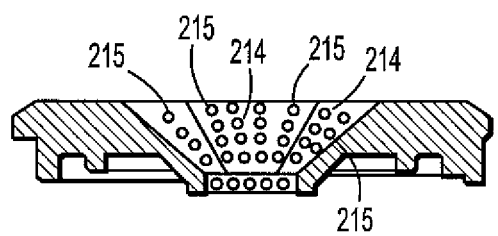

FIGS. 4-6 illustrate an alternate embodiment of cover 206 of a seal assembly. In accordance with this embodiment, cover 206 includes a plurality, e.g., three, of intersecting entry surfaces 214 obliquely arranged relative to the seal axis and extending from proximal or entry opening 210 to distal or exit opening 212 of the cover 206. Entry surfaces 214 may be planar or arcuate and function to direct the instrument though distal opening 212 of cover 206. Entry surfaces 214 may be disposed in various angular relationships creating differing guidance pathways. FIGS. 7-9 illustrate cover 206 with four intersecting entry surfaces 214 and FIGS. 10-12 illustrate cover 206 with six intersecting entry surfaces 214. It is envisioned that any number of entry surfaces 214 may be incorporated into cover 206.

In embodiments, the entry surfaces 214 of cover 206 may possess a patterned coating of the present disclosure on at least a portion thereon. An example of such an cover possessing such a coating is set forth in FIG. 12. As can be seen in FIG. 12, cover 206 may possess a lubricious coating possessing a dot matrix pattern with a plurality of dots 215 on entry surface 214 thereof.

Figure 13:
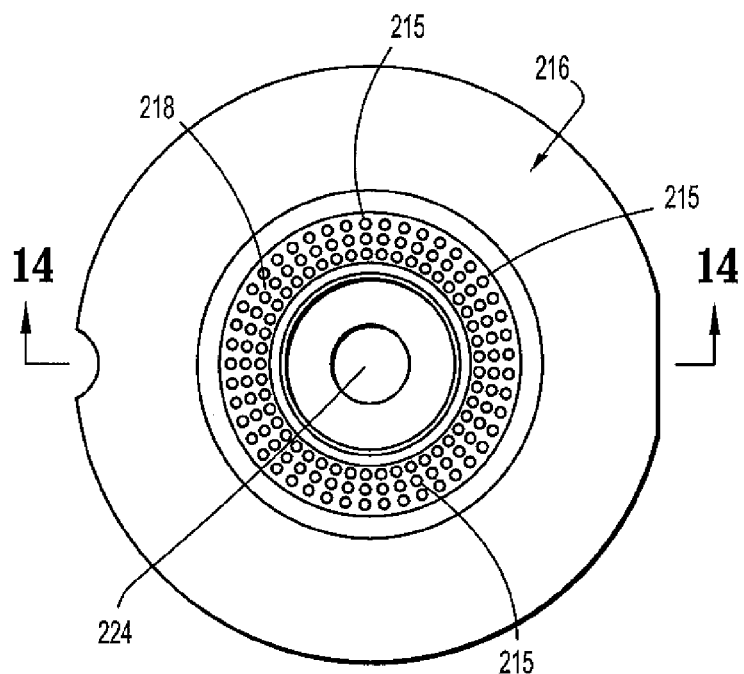
FIG. 13 is a top plan of a resilient seal which may be utilized with the seal assembly.
Figure 14:
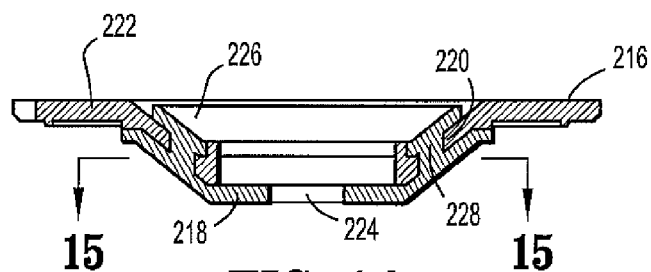
FIG. 14 is a cross-sectional view of the seal mount and resilient seal of the seal assembly taken along the lines 17-17 of FIG. 13.
Figure 15:
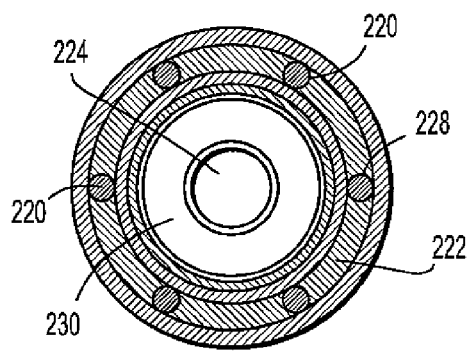
FIG. 15 is a top view of an integrally coupled seal mount and resilient seal thereby forming the seal assembly.

Referring now to FIGS. 13-15, seal 204 may include annular seal mount 216 and resilient seal 218 connected to the mount 216. Seal mount 216 may be formed of a relatively rigid material such as a suitable polymeric material or alternatively may be fabricated from a resilient material. Seal mount 216 incorporates a plurality of apertures 220 extending through wall 222 of the seal mount 216. Resilient seal 218 defines aperture 224 and is arranged to form a substantial seal about an instrument inserted therethrough. In some embodiments, resilient seal 218 may be adapted to form a seal about an instrument having a diameter from about 3 mm to about 7 mm, in embodiments about 5 mm. In this regard, aperture 224 of seal 218 defines a diameter of from about 2 mm to about 3 mm. Seal 218 may be formed of any suitable elastomeric material. In some embodiments, seal 218 may be integrally formed with seal mount 216 such that the elastomeric material communicates through apertures 220 to form the integrally coupled unit depicted in FIGS. 14-15. Seal mount 216 and seal 218 may be co-molded utilizing means within the purview of those skilled in the art. In embodiments, seal 218 may be molded with seal mount 216 to provide annular entry seal portion 226, anchoring segments or spokes 228 extending through apertures 220 of seal mount 216 and planar inner seal portion 230. Annular entry seal portion 226 may define a general frusto-conical configuration and provides an engagement area which may support cover 206 and may form a fluid-tight seal with the cover 200. Inner seal portion 230 may define aperture 224.

Seal 218 may be a fabric seal as disclosed in U.S. Pat. No. 6,702,787, the entire disclosure of which is incorporated by reference herein. The seal disclosed in U.S. Pat. No. 6,702,787 may be a flat septum seal having a first layer of resilient material and at least one fabric layer juxtaposed relative to the first layer. The fabric layer may include a SPANDEX material containing from about 16% to about 22% LYCRA from Milliken. Other arrangements for seal 218 are also envisioned. Seal 218 may be flat, hemispherical or have any other shape as desired. In embodiments, seal mount 216 may possess a shape corresponding to the shape of seal 218.

The seal may possess a patterned coating of the present disclosure on a portion of its surface to enhance passage of a cannula therethrough. An example of such a seal possessing such a patterned coating is set forth in FIG. 13. As can be seen in FIG. 13, seal 218 may possess a lubricious coating possessing a dot matrix pattern with a plurality of dots 215 on a surface thereof. Similarly, the cannula may possess a patterned coating of the present disclosure on a portion of its surface to enhance passage of the cannula through the seal.

In use, a surgeon places a cannula assembly through a body wall in a conventional manner such that a port of entry for surgical instrumentation is established. The surgeon may utilize instrumentation sized to cooperate with the cannula assembly, and particularly the seal assembly of the selected cannula assembly, without loss of pneumoperitoneum gas. If not already secured, seal assembly may be secured to cannula assembly. Thereafter, the surgeon introduces an instrument, e.g., 5 mm instrument through seal assembly while the seal forms a seal about the instrument. If the surgeon desires to use an instrument of diameter which is smaller than the seal assembly is designed to accommodate, an adapter body may be positioned over the seal housing and secured to outer surface of the seal housing. The surgeon proceeds with the surgical procedure by inserting surgical instrument(s) of suitable diameter through the seal and any adapter seal, if necessary, thus sealingly engaging the surgical instrument, thereby providing a gas seal therebetween.

Coatings of the present disclosure avoid delamination and/or fracturing which might otherwise occur as the substrate flexes or undergoes any similar mechanical change, including bending, elongation or stretching, combinations thereof, and the like.

It will be understood that various modifications may be made to the embodiments disclosed herein. Therefore, the above description should not be construed as limiting, but merely as exemplifications of embodiments of the present disclosure. Those skilled in the art will envision other modifications within the scope and spirit of the claims appended hereto.

What is claimed:

1. A method for manufacturing a seal, comprising:
providing a seal;
applying a patterned lubricious coating in a dot matrix pattern on at least a portion of the seal to lower the coefficient of friction of the seal, the dot matrix pattern including a plurality of cured dots, each dot being devoid of interconnection with the other dots of the dot matrix pattern.

2. The method of claim 1, wherein the coating is selected from the group consisting of cyanoacrylates, epoxies, hydrophilic polymers, hydrogels, polyalkylene oxides, urethanes, polyurethanes, siloxanes, cyclosiloxanes, polyalkylsiloxanes, polydialkylsiloxanes, parylenes, and combinations thereof.

3. The method of claim 1, wherein the coating is selected from the group consisting of polyethylene oxide, polypropylene oxide, polyethylene oxide/polypropylene oxide copolymers, polyethylene glycol, polypropylene glycol, polydimethylsiloxanes, polydiethylsiloxanes, polydipropylsiloxanes, polydibutylsiloxanes, parylene N, parylene C, parylene D, parylene HT, and combinations thereof.

4. The method of claim 1, wherein the coating is applied by a method selected from the group consisting of gravure coating, spray coating, melt blowing, flexographic printing, screen printing, and combinations thereof.

5. The method of claim 1, wherein the coating is applied in powder form.

6. The method of claim 1, wherein the coating is applied as a coating solution including a solvent selected from the group consisting of tetrahydrofuran, methylene chloride, methanol, ethanol, propanol, chloroform, 1,2-dichloro-ethane, hexane, heptene, ethyl acetate, and combinations thereof.

7. The method of claim 6, wherein the coating solution comprises from about 30 to about 70 weight percent solvent.

8. The method of claim 1, further comprising heating the coating to a temperature from about 80° F. to about 350° F.

9. The method of claim 1, wherein the seal possesses a coating-free surface area from about 75% to about 99%.

10. The method of claim 1, wherein a dot of the dot matrix pattern has a ratio of height to diameter from about 0.05:1 to about 2:1.

11. The method of claim 1, further comprising enabling the seal to receive an object in a substantially sealed relationship with the object such that the coating facilitates reception of the object.

12. The method of claim 1, further comprising providing at least one of the dots with a substantially polygonal shape.

13. The method of claim 1, further comprising providing at least one of the dots with a substantially circular shape.

14. The method of claim 1, further comprising providing at least some of the dots lined in rows.

15. The method of claim 14, further comprising offsetting adjacent rows.

16. The method of claim 1, further comprising disposing a plurality of the dots in a random pattern.

* * * * *